US008442287B2

(12) United States Patent
Fordyce, II et al.

(10) Patent No.: US 8,442,287 B2
(45) Date of Patent: May 14, 2013

(54) METHOD AND SYSTEM FOR EVALUATING QUALITY ASSURANCE CRITERIA IN DELIVERY OF A TREATMENT PLAN

(75) Inventors: Gerald D. Fordyce, II, Madison, WI (US); Kenneth J. Ruchala, Madison, WI (US); Eric Schnarr, McFarland, WI (US); Yu Chen, Madison, WI (US); Graham T. Reitz, Madison, WI (US); Scott Finley, Madison, WI (US); Rob O'Connell, Madison, WI (US); Matthew Orton, Oregon, WI (US)

(73) Assignee: Tomotherapy Incorporated, Madison, WI (US)

( * ) Notice: Subject to any disclaimer, the term of this patent is extended or adjusted under 35 U.S.C. 154(b) by 374 days.

(21) Appl. No.: 12/854,139

(22) Filed: Aug. 10, 2010

(65) Prior Publication Data
US 2011/0112351 A1 May 12, 2011

Related U.S. Application Data

(63) Continuation-in-part of application No. 11/459,152, filed on Jul. 21, 2006, now Pat. No. 7,773,788.

(60) Provisional application No. 60/701,580, filed on Jul. 22, 2005.

(51) Int. Cl.
*G06K 9/00* (2006.01)

(52) U.S. Cl.
USPC ............ 382/128; 382/131; 382/132; 600/427

(58) Field of Classification Search .................. 382/128, 382/131, 132; 600/427
See application file for complete search history.

(56) References Cited

U.S. PATENT DOCUMENTS

| | | | |
|---|---|---|---|
| 3,949,265 | A | 4/1976 | Holl |
| 3,964,467 | A | 6/1976 | Rose |

(Continued)

FOREIGN PATENT DOCUMENTS

| | | |
|---|---|---|
| CA | 2091275 | 9/1993 |
| JP | 63209667 | 8/1988 |

(Continued)

OTHER PUBLICATIONS

Purdy, James, "3D Treatment Planning and Intensity-Modulated Radiation Therapy," Oncology, vol. 13, No. 10, suppl. 5 (Oct. 1999).

(Continued)

*Primary Examiner* — John Strege
(74) *Attorney, Agent, or Firm* — Michael Best & Friedrich LLP

(57) ABSTRACT

System and method of determining whether a component of a radiation therapy system is operating within a dosimetric tolerance. The method can include the acts of generating a treatment plan for a patient, the treatment plan specifying a radiation amount to be delivered to the patient, delivering radiation to the patient according to the treatment plan, obtaining feedback during the delivery of radiation, the feedback related to one of a position, a velocity, and an acceleration for one of a multi-leaf collimator, a gantry, a couch, and a jaws, generating a mathematical model based on the feedback for one of the multi-leaf collimator, the gantry, the couch, and the jaws, calculating a delivered dose amount based on the mathematical model and treatment plan information, calculating a deviation in dose between the radiation amount specified in the treatment plan and the delivered dose amount, and determining whether the deviation in dose is within a dosimetric tolerance for the one of the multi-leaf collimator, the gantry, the couch, and the jaws.

2 Claims, 6 Drawing Sheets

U.S. PATENT DOCUMENTS

| | | |
|---|---|---|
| 4,006,422 A | 2/1977 | Schriber |
| 4,032,810 A | 6/1977 | Eastham et al. |
| 4,149,081 A | 4/1979 | Seppi |
| 4,181,894 A | 1/1980 | Pottier |
| 4,189,470 A | 2/1980 | Rose |
| 4,208,185 A | 6/1980 | Sawai et al. |
| 4,273,867 A | 6/1981 | Lin et al. |
| 4,314,180 A | 2/1982 | Salisbury |
| 4,335,465 A | 6/1982 | Christiansen et al. |
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,455,609 A | 6/1984 | Inamura et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,027,818 A | 7/1991 | Bova et al. |
| 5,044,354 A | 9/1991 | Goldhorn et al. |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,117,829 A | 6/1992 | Miller et al. |
| 5,124,658 A | 6/1992 | Adler |
| 5,138,647 A | 8/1992 | Nguyen et al. |
| 5,210,414 A | 5/1993 | Wallace et al. |
| 5,250,388 A | 10/1993 | Schoch, Jr. et al. |
| 5,317,616 A | 5/1994 | Swerdloff et al. |
| 5,332,908 A | 7/1994 | Weidlich |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,446,548 A | 8/1995 | Gerig et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,511,549 A | 4/1996 | Legg et al. |
| 5,523,578 A | 6/1996 | Herskovic |
| 5,528,650 A | 6/1996 | Swerdoloff et al. |
| 5,548,627 A | 8/1996 | Swerdoloff et al. |
| 5,552,605 A | 9/1996 | Arata |
| 5,576,602 A | 11/1996 | Hiramoto et al. |
| 5,578,909 A | 11/1996 | Billen |
| 5,579,358 A | 11/1996 | Lin |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,811,944 A | 9/1998 | Sampayan et al. |
| 5,815,547 A | 9/1998 | Shepherd et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,823,192 A | 10/1998 | Kalend et al. |
| 5,834,454 A | 11/1998 | Kitano et al. |
| 5,835,562 A | 11/1998 | Ramsdell et al. |
| 5,836,905 A | 11/1998 | Lemelson et al. |
| 5,842,175 A | 11/1998 | Andros et al. |
| 5,866,912 A | 2/1999 | Slater et al. |
| 5,870,447 A | 2/1999 | Powell et al. |
| 5,877,023 A | 3/1999 | Sautter et al. |
| 5,877,192 A | 3/1999 | Lindberg et al. |
| 5,901,199 A | 5/1999 | Murphy et al. |
| 5,907,594 A | 5/1999 | Lai |
| 5,912,134 A | 6/1999 | Shartle |
| 5,920,601 A | 7/1999 | Nigg et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,144,875 A | 11/2000 | Schweikard et al. |
| 6,152,599 A | 11/2000 | Salter, Jr. |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |
| 6,218,675 B1 | 4/2001 | Akiyama et al. |
| 6,222,905 B1 | 4/2001 | Yoda et al. |
| 6,241,670 B1 | 6/2001 | Nambu |
| 6,242,747 B1 | 6/2001 | Sugitani et al. |
| 6,260,005 B1 | 7/2001 | Yang et al. |
| 6,264,825 B1 | 7/2001 | Blackburn et al. |
| 6,265,837 B1 | 7/2001 | Akiyama et al. |
| 6,279,579 B1 | 8/2001 | Riaziat et al. |
| 6,291,823 B1 | 9/2001 | Doyle et al. |
| 6,301,329 B1 | 10/2001 | Surridge |

| | | |
|---|---|---|
| 6,316,776 B1 | 11/2001 | Hiramoto et al. |
| 6,319,469 B1 | 11/2001 | Mian et al. |
| 6,322,249 B1 | 11/2001 | Wofford et al. |
| 6,331,194 B1 | 12/2001 | Sampayan et al. |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,407,505 B1 | 6/2002 | Bertsche |
| 6,417,178 B1 | 7/2002 | Klunk et al. |
| 6,424,856 B1 | 7/2002 | Vilsmeier et al. |
| 6,428,547 B1 | 8/2002 | Vilsmeier et al. |
| 6,433,349 B2 | 8/2002 | Akiyama et al. |
| 6,438,202 B1 | 8/2002 | Olivera et al. |
| 6,455,844 B1 | 9/2002 | Meyer |
| 6,462,490 B1 | 10/2002 | Matsuda et al. |
| 6,465,957 B1 | 10/2002 | Whitham et al. |
| 6,466,644 B1 | 10/2002 | Hughes et al. |
| 6,469,058 B1 | 10/2002 | Grove et al. |
| 6,472,834 B2 | 10/2002 | Hiramoto et al. |
| 6,473,490 B1 | 10/2002 | Siochi |
| 6,475,994 B2 | 11/2002 | Tomalia et al. |
| 6,482,604 B2 | 11/2002 | Kwon |
| 6,484,144 B2 | 11/2002 | Martin et al. |
| 6,487,274 B2 | 11/2002 | Bertsche |
| 6,493,424 B2 | 12/2002 | Whitham |
| 6,497,358 B1 | 12/2002 | Walsh |
| 6,498,011 B2 | 12/2002 | Hohn et al. |
| 6,500,343 B2 | 12/2002 | Siddiqi |
| 6,504,899 B2 | 1/2003 | Pugachev et al. |
| 6,510,199 B1 | 1/2003 | Hughes et al. |
| 6,512,942 B1 | 1/2003 | Burdette et al. |
| 6,516,046 B1 | 2/2003 | Frohlich et al. |
| 6,527,443 B1 | 3/2003 | Vilsmeier et al. |
| 6,531,449 B2 | 3/2003 | Khojasteh et al. |
| 6,535,837 B1 | 3/2003 | Schach Von Wittenau |
| 6,539,247 B2 | 3/2003 | Spetz |
| 6,552,338 B1 | 4/2003 | Doyle |
| 6,558,961 B1 | 5/2003 | Sarphie et al. |
| 6,560,311 B1 | 5/2003 | Shepard et al. |
| 6,562,376 B2 | 5/2003 | Hooper et al. |
| 6,568,449 B2 | 5/2003 | Owen et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,617,768 B1 | 9/2003 | Hansen |
| 6,618,467 B1 | 9/2003 | Ruchala et al. |
| 6,621,889 B1 | 9/2003 | Mostafavi |
| 6,633,686 B1 | 10/2003 | Bakircioglu et al. |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,661,870 B2 | 12/2003 | Kapatoes et al. |
| 6,687,654 B2 | 2/2004 | Smith et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,719,683 B2 | 4/2004 | Frohlich |
| 6,723,334 B1 | 4/2004 | McGee et al. |
| 6,731,970 B2 | 5/2004 | Schlossbauer et al. |
| 6,741,674 B2 | 5/2004 | Lee |
| 6,757,355 B1 | 6/2004 | Siochi |
| 6,760,402 B2 | 7/2004 | Ghelmansarai |
| 6,774,383 B2 | 8/2004 | Norimine et al. |
| 6,787,771 B2 | 9/2004 | Bashkirov et al. |
| 6,787,983 B2 | 9/2004 | Yamanobe et al. |
| 6,788,764 B2 | 9/2004 | Saladin et al. |
| 6,792,073 B2 | 9/2004 | Deasy et al. |
| 6,792,074 B2 | 9/2004 | Erbel et al. |
| 6,796,164 B2 | 9/2004 | McLoughlin et al. |
| 6,800,866 B2 | 10/2004 | Amemiya et al. |
| 6,804,548 B2 | 10/2004 | Takahashi et al. |
| 6,810,107 B2 | 10/2004 | Steinberg |
| 6,822,244 B2 | 11/2004 | Beloussov et al. |
| 6,822,247 B2 | 11/2004 | Sasaki |
| 6,838,676 B1 | 1/2005 | Jackson |
| 6,842,502 B2 | 1/2005 | Jaffray et al. |
| 6,844,689 B1 | 1/2005 | Brown et al. |
| 6,853,702 B2 | 2/2005 | Renner |
| 6,865,253 B2 | 3/2005 | Blumhofer et al. |
| 6,865,411 B2 | 3/2005 | Erbel et al. |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,889,695 B2 | 5/2005 | Pankratov et al. |
| 6,891,178 B2 | 5/2005 | Xing |
| 6,898,456 B2 | 5/2005 | Erbel |
| 6,904,125 B2 | 6/2005 | Van Dyk et al. |
| 6,907,282 B2 | 6/2005 | Siochi |
| 6,922,455 B2 | 7/2005 | Jurczyk et al. |
| 6,929,398 B1 | 8/2005 | Tybinkowski et al. |
| 6,936,832 B2 | 8/2005 | Norimine et al. |
| 6,955,464 B1 | 10/2005 | Tybinkowski et al. |
| 6,961,405 B2 | 11/2005 | Scherch |
| 6,963,171 B2 | 11/2005 | Sagawa et al. |
| 6,963,771 B2 | 11/2005 | Scarantino et al. |
| 6,974,254 B2 | 12/2005 | Paliwal et al. |
| 6,977,984 B2 | 12/2005 | Hsieh et al. |
| 6,984,835 B2 | 1/2006 | Harada |
| 6,990,167 B2 | 1/2006 | Chen |
| 7,015,490 B2 | 3/2006 | Wang et al. |
| 7,046,762 B2 | 5/2006 | Lee |
| 7,046,831 B2 | 5/2006 | Ruchala et al. |
| 7,051,605 B2 | 5/2006 | Lagraff et al. |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,087,200 B2 | 8/2006 | Taboas et al. |
| 7,092,482 B2 | 8/2006 | Besson |
| 7,112,924 B2 | 9/2006 | Hanna |
| 7,130,372 B2 | 10/2006 | Kusch et al. |
| 7,154,991 B2 | 12/2006 | Earnst et al. |
| 7,158,692 B2 | 1/2007 | Chalana et al. |
| 7,186,986 B2 | 3/2007 | Hinderer et al. |
| 7,186,991 B2 | 3/2007 | Kato et al. |
| 7,203,272 B2 | 4/2007 | Chen |
| 7,209,547 B2 | 4/2007 | Baier et al. |
| 7,221,733 B1 | 5/2007 | Takai et al. |
| 7,252,307 B2 | 8/2007 | Kanbe et al. |
| 7,257,196 B2 | 8/2007 | Brown et al. |
| 7,280,630 B2 | 10/2007 | Chen |
| 7,333,588 B2 | 2/2008 | Mistretta et al. |
| 7,367,955 B2 | 5/2008 | Zhang et al. |
| 7,391,026 B2 | 6/2008 | Trinkaus et al. |
| 7,412,029 B2 | 8/2008 | Myles |
| 7,413,873 B2 | 8/2008 | Waterman et al. |
| 7,450,687 B2 | 11/2008 | Yeo et al. |
| 7,492,858 B2 | 2/2009 | Partain et al. |
| 7,496,173 B2 | 2/2009 | Goldman et al. |
| 7,508,967 B2 | 3/2009 | Harari et al. |
| 7,519,150 B2 | 4/2009 | Romesberg et al. |
| 7,551,717 B2 | 6/2009 | Tome et al. |
| 7,567,694 B2 | 7/2009 | Lu et al. |
| 7,574,251 B2 | 8/2009 | Lu et al. |
| 7,609,809 B2 | 10/2009 | Kapatoes et al. |
| 7,629,599 B2 | 12/2009 | Hashimoto |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,773,788 B2 | 8/2010 | Lu et al. |
| 7,831,289 B2 | 11/2010 | Riker et al. |
| 7,839,972 B2 | 11/2010 | Ruchala et al. |

| | | |
|---|---|---|
| 7,945,022 B2 | 5/2011 | Nelms et al. |
| 7,957,507 B2 | 6/2011 | Cadman |
| 7,983,380 B2 | 7/2011 | Guertin et al. |
| 8,073,104 B2 | 12/2011 | Yan et al. |
| 8,085,899 B2 | 12/2011 | Nord et al. |
| 2002/0193685 A1 | 12/2002 | Mate et al. |
| 2003/0086527 A1 | 5/2003 | Speiser et al. |
| 2003/0095625 A1 | 5/2003 | Steinberg |
| 2003/0105650 A1 | 6/2003 | Lombardo et al. |
| 2004/0010418 A1 | 1/2004 | Buonocore et al. |
| 2004/0024300 A1 | 2/2004 | Graf |
| 2004/0068182 A1 | 4/2004 | Misra |
| 2004/0116804 A1 | 6/2004 | Mostafavi |
| 2004/0254773 A1 | 12/2004 | Zhang et al. |
| 2005/0031181 A1 | 2/2005 | Bi et al. |
| 2005/0080332 A1 | 4/2005 | Shiu et al. |
| 2005/0096515 A1 | 5/2005 | Geng |
| 2005/0143965 A1 | 6/2005 | Failla et al. |
| 2005/0180544 A1 | 8/2005 | Sauer et al. |
| 2005/0197564 A1 | 9/2005 | Dempsey |
| 2005/0201516 A1 | 9/2005 | Ruchala et al. |
| 2005/0251029 A1 | 11/2005 | Khamene et al. |
| 2006/0074292 A1 | 4/2006 | Thomson et al. |
| 2006/0100738 A1 | 5/2006 | Alsafadi et al. |
| 2006/0133568 A1 | 6/2006 | Moore |
| 2006/0241332 A1 | 10/2006 | Klein et al. |
| 2006/0285639 A1 | 12/2006 | Olivera et al. |
| 2006/0285640 A1 | 12/2006 | Nizin et al. |
| 2007/0041496 A1 | 2/2007 | Olivera et al. |
| 2007/0041498 A1 | 2/2007 | Olivera et al. |
| 2007/0041500 A1 | 2/2007 | Olivera et al. |
| 2007/0076846 A1 | 4/2007 | Ruchala et al. |
| 2007/0088573 A1 | 4/2007 | Ruchala et al. |
| 2007/0104316 A1 | 5/2007 | Ruchala et al. |
| 2007/0127790 A1 | 6/2007 | Lau et al. |
| 2007/0195922 A1 | 8/2007 | Mackie et al. |
| 2007/0197908 A1 | 8/2007 | Ruchala et al. |
| 2007/0201613 A1 | 8/2007 | Lu et al. |
| 2007/0211857 A1 | 9/2007 | Urano et al. |
| 2008/0002809 A1 | 1/2008 | Bodduluri |
| 2008/0002811 A1 | 1/2008 | Allison |
| 2008/0008291 A1 | 1/2008 | Alakuijala et al. |
| 2008/0031406 A1 | 2/2008 | Yan et al. |
| 2008/0049896 A1 | 2/2008 | Kuduvalli |
| 2008/0064953 A1 | 3/2008 | Falco et al. |
| 2008/0279328 A1 | 11/2008 | Zeitler et al. |
| 2009/0041200 A1 | 2/2009 | Lu et al. |
| 2009/0110145 A1 | 4/2009 | Lu et al. |
| 2009/0116616 A1 | 5/2009 | Lu et al. |
| 2009/0121144 A1 | 5/2009 | Black et al. |
| 2009/0252291 A1 | 10/2009 | Lu et al. |
| 2010/0053208 A1 | 3/2010 | Menningen et al. |
| 2010/0054413 A1 | 3/2010 | Sobering et al. |
| 2011/0019889 A1 | 1/2011 | Gering et al. |

FOREIGN PATENT DOCUMENTS

| | | |
|---|---|---|
| JP | 6007464 | 1/1994 |
| JP | 10052421 | 2/1998 |
| JP | 10501151 | 2/1998 |
| JP | 11244401 | 9/1999 |
| JP | 2000116643 | 4/2000 |
| JP | 2001340474 | 12/2001 |
| JP | 2002210029 | 7/2002 |
| JP | 2002522128 | 7/2002 |
| JP | 2002522129 | 7/2002 |
| JP | 2003523220 | 8/2003 |
| JP | 2004166975 | 6/2004 |
| JP | 2004275636 | 10/2004 |
| JP | 2004321502 | 11/2004 |
| JP | 2005160804 | 6/2005 |
| JP | 2005518908 | 6/2005 |
| JP | 2007509644 | 4/2007 |
| JP | 2007516743 | 6/2007 |
| TW | 300853 | 3/1997 |
| WO | 9014129 | 11/1990 |
| WO | 9202277 | 2/1992 |
| WO | 9802091 | 1/1998 |
| WO | 0007669 | 2/2000 |
| WO | 0054689 | 9/2000 |
| WO | 03076003 | 9/2003 |
| WO | 03092789 | 11/2003 |
| WO | 2004057515 | 7/2004 |
| WO | 2004105574 | 12/2004 |
| WO | 2005031629 | 4/2005 |
| WO | 2005057463 | 6/2005 |

OTHER PUBLICATIONS

Bertalmio, Marcelo, et al., "Morphing Active Contours", IEEE Transactions on Pattern Analysis and Machine Intelligence, vol. 22, No. 7, pp. 733-737, Jul. 2000.

Yu, Cedric X., et al., "A Method for Implementing Dynamic Photon Beam Intensity Modulation using Independent Jaws and a Multileaf Collimator," Phys. Med. Biol. 40. 1995: 769-787.

Keall, Paul, "4-Dimensional Computed Tomography Imaging and Treatment Planning," Seminars in Radiation Oncology, vol. 14, No. 1, Jan. 2004; pp. 81-90.

Lu, W., et al., "Automatic Re-Contouring Regions of Interest Based on Deformable Registration and Surface Reconstruction," AAPM 2004, (abstract: Medical Physics 31, 1845-6).

Lu, W., et al., "Automatic Re-Contouring in 4D Radiotherapy", Physical Medical Biology, Mar. 7, 2006, 51 (5):1077-99.

Lu, W., et al., 2004 "Automatic Re-Contouring for 4-D Planning and Adaptive Radiotherapy," The 90th RSNA Meeting, Chicago, Illinois, (abstract:Radiology 227 (p. 543).

Mackie, T. Rockwell et al., "Tomotherapy" Seminars in Radiation Oncology, vol. 9, No. 1, Jan. 1, 1999, pp. 108-117, XP002603992.

Ruchala, Kenneth, et al., "Adaptive IMRT with Tomotherapy", RT Image, vol. 14, No. 25, pp. 14-18, Jun. 18, 2001.

Rueckert, D.et al., "Nonrigid Registration Using Free-Form Deformations: Application to Breast MR Images", IEEE Transactions on Medical Imaging, vol. 18, No. 8, pp. 712-721, Aug. 1999.

Yezzi, et al., "A Variational Framework for Joint Segmentation and Registration", Mathematical Method in Biomedical Image Analysis, 8 pages, 2001.

Young, Yuan-Nan, et al., "Registration-Based Morphing of Active Contours for Segmentation of CT Scans", Mathematical Biosciences and Engineering, vol. 2, No. 1, pp. 79-96, Jan. 2005.

Office Action from Chinese Patent Office for Application No. 200680034597.5 dated Aug. 14, 2009.

Office Action from Chinese Patent Office for Application No. 200680034597.5 dated Dec. 24, 2010.

Office Action from European Patent Office for Application No. 06800246.8 dated Aug. 6, 2010.

Office Action from European Patent Office for Application No. 06800246.8 dated Feb. 25, 2011.

Extended Search Report from European Patent Office for Application No. 06800246.8 dated Sep. 23, 2009.

PCT/US2006/028556 International Search Report and Written Opinion mailed Jul. 10, 2007.

PCT/US2011/047103 International Search Report and Written Opinion dated Mar. 9, 2012.

Search Report from Taiwan Patent Office for Application No. 095127022 dated Aug. 6, 2010.

Office Action from Chinese Patent Office for Application No. 200680034597.5 dated Jun. 15, 2011.

Office Action from Japanese Patent Office for Application No. 2008-523026 dated Jan. 5, 2012.

Mackie, T. Rockwell et al., "Tomotherapy: Rethinking the Processes of Radiotherapy," XIIth ICCR, May 27-30, 1997.

Fang, Guang Y. et al., "Software system for the UW/GE tomotherapy prototype," Xiith ICCR, May 27-30, 1997.

Office Action from European Patent Office for Application No. 06800246.8 dated Mar. 26, 2012.

METHOD AND SYSTEM FOR EVALUATING QUALITY ASSURANCE CRITERIA IN DELIVERY OF A TREATMENT PLAN

RELATED APPLICATIONS

This application is a continuation-in-part of and claims priority to U.S. patent application Ser. No. 11/459,152, filed on Jul. 21, 2006, which is a non-provisional of and claims priority to U.S. Provisional Patent Application No. 60/701,580, filed on Jul. 22, 2005, titled SYSTEM AND METHOD FOR FEEDBACK GUIDED QUALITY ASSURANCE AND ADAPTATIONS TO RADIATION THERAPY TREATMENT. The entire contents of these application are incorporated herein by reference.

BACKGROUND OF THE INVENTION

Over the past decades improvements in computers and networking, radiation therapy treatment planning software, and medical imaging modalities (CT, MRI, US, and PET) have been incorporated into radiation therapy practice. These improvements have led to the development of image guided radiation therapy ("IGRT"). IGRT is radiation therapy that uses cross-sectional images of the patient's internal anatomy to better target the radiation dose in the tumor while reducing the radiation exposure to healthy organs. The radiation dose delivered to the tumor is controlled with intensity modulated radiation therapy ("IMRT"), which involves changing the size, shape, and intensity of the radiation beam to conform to the size, shape, and location of the patient's tumor. IGRT and IMRT lead to improved control of the tumor while simultaneously reducing the potential for acute side effects due to irradiation of healthy tissue surrounding the tumor.

IMRT is becoming the standard of care in several countries. However, in many situations, IMRT is not used to treat a patient due to time, resources, and billing constraints. Daily images of the patient can be used to guarantee that the high gradients generated by IMRT plans are located on the correct position for patient treatment. Also these images can provide necessary information to adapt the plan online or offline if needed.

It is commonly known in the field of radiation therapy that there are many sources of uncertainty and change that can occur during a course of a patient's treatment. Some of these sources represent random errors, such as small differences in a patient's setup position each day. Other sources are attributable to physiological changes, which might occur if a patient's tumor regresses or the patient loses weight during therapy. A third possible category regards motion. Motion can potentially overlap with either of the other categories, as some motion might be more random and unpredictable, such as a patient coughing or passing gas, whereas other motion can be more regular, such as breathing motion, sometimes.

SUMMARY OF THE INVENTION

In radiation therapy, uncertainties can affect the quality of a patient's treatment. For example, when delivering a treatment dose to a target region, it is standard practice to also treat a high-dose "margin" region about the target. This helps ensure that the target receives the desired dose, even if its location changes during the course of the treatment, or even during a single fraction. The less definite a target's location, the larger the margins that typically need to be used.

Adaptive radiation therapy generally refers to the concept of using feedback during the course of radiation therapy treatment to improve future treatments. Feedback can be used in off-line adaptive therapy processes and on-line adaptive therapy processes. Off-line adaptive therapy processes occur while the patient is not being treated, such as in between treatment fractions. In one version of this, during each fraction, a new CT image of the patient is acquired before or after each of the fractions. After the images are acquired from the first few treatment fractions, the images are evaluated to determine an effective envelope of the multi-day locations of target structures. A new plan can then be developed to better reflect the range of motion of the target structure, rather than using canonical assumptions of motion. A more complex version of off-line adaptive therapy is to recalculate the delivered dose after each fraction and accumulate these doses, potentially utilizing deformation techniques, during this accumulation to account for internal motion. The accumulated dose can then be compared to the planned dose, and if any discrepancies are noted, subsequent fractions can be modified to account for the changes.

On-line adaptive therapy processes typically occur while the patient is in the treatment room, and potentially, but not necessarily, during a treatment delivery. For example, some radiation therapy treatment systems are equipped with imaging systems, such as on-line CT or x-ray systems. These systems can be used prior to treatment to validate or adjust the patient's setup for the treatment delivery. The imaging systems may also be used to adapt the treatment during the actual treatment delivery. For example, an imaging system potentially can be used concurrently with treatment to modify the treatment delivery to reflect changes in patient anatomy.

One aspect of the present invention is to disclose new opportunities for the application of adaptive therapy techniques, and additional aspects are to present novel methods for adaptive therapy. In particular, adaptive therapy has typically focused on feedback to modify a patient's treatment, but the present invention focuses on adaptive therapy processes being used in a quality assurance context. This is particularly true in the context of whole-system verification.

For example, a detector can be used to collect information indicating how much treatment beam has passed through the patient, from which the magnitude of the treatment output can be determined as well as any radiation pattern that was used for the delivery. The benefit of this delivery verification process is that it enables the operator to detect errors in the machine delivery, such as an incorrect leaf pattern or machine output.

However, validating that the machine is functioning properly does not itself ensure proper delivery of a treatment plan, as one also needs to validate that the external inputs used to program the machine are effective and consistent. Thus, one aspect of the invention includes the broader concept of an adaptive-type feedback loop for improved quality assurance of the entire treatment process. In this aspect, the invention includes the steps of positioning the patient for treatment and using a method for image-guidance to determine the patient's position, repositioning the patient as necessary for treatment based upon the image-guidance, and beginning treatment. Then, either during or after treatment, recalculating the patient dose and incorporating the patient image information that had been collected before or during treatment. After completion of these steps, quality assurance data is collected to analyze the extent to which the delivery was not only performed as planned, but to validate that the planned delivery is reasonable in the context of the newly available data. In this regard, the concept of feedback is no longer being used to indicate changes to the treatment based on changes in the patient or delivery, but to validate the original delivery itself.

As an example, it is possible that a treatment plan might be developed for a patient, but that the image used for planning became corrupted, such as by applying an incorrect density calibration. In this case, the treatment plan will be based upon incorrect information, and might not deliver the correct dose to the patient. Yet, many quality assurance techniques will not detect this error because they will verify that the machine is operating as instructed, rather than checking whether the instructions to the machine are based on correct input information. Likewise, some adaptive therapy techniques could be applied to this delivery, but if the calibration problem of this example persisted, then the adapted treatments would suffer from similar flaws.

There are a number of processes that can be used to expand the use of feedback for quality assurance purposes. For example, in one embodiment, this process would include the delivery verification techniques described above. The validation of machine performance that these methods provide is a valuable component of a total-system quality assurance toolset. Moreover, the delivery verification processes can be expanded to analyze other system errors, such as deliveries based on images with a truncated field-of-view.

In one embodiment, the invention provides a method of determining whether a component of a radiation therapy system is operating within a dosimetric tolerance. The method comprises generating a treatment plan for a patient, the treatment plan specifying a radiation amount to be delivered to the patient, delivering radiation to the patient according to the treatment plan, obtaining feedback during the delivery of radiation, the feedback related to one of a position, a velocity, and an acceleration for one of a multi-leaf collimator, a gantry, a couch, and a jaws, generating a mathematical model based on the feedback for one of the multi-leaf collimator, the gantry, the couch, and the jaws, calculating a delivered dose amount based on the mathematical model and treatment plan information, calculating a deviation in dose between the radiation amount specified in the treatment plan and the delivered dose amount, and determining whether the deviation in dose is within a dosimetric tolerance for the one of the multi-leaf collimator, the gantry, the couch, and the jaws.

In another embodiment, the invention provides a method of determining whether a component of a radiation therapy system deviated from specified operation. The method comprises generating a treatment plan for a patient, the treatment plan specifying a radiation amount to be delivered to the patient, delivering radiation to the patient according to the treatment plan, obtaining feedback during the delivery of radiation, the feedback related to one of a position, a velocity, and an acceleration for one of a multi-leaf collimator, a gantry, a couch, and a jaws, calculating a delivered dose amount based on the feedback, calculating a deviation in dose between the radiation amount specified in the treatment plan and the delivered dose amount, and adjusting one of the multi-leaf collimator, the gantry, the couch, and the jaws to minimize the deviation in dose.

Other aspects of the invention will become apparent by consideration of the detailed description and accompanying drawings.

DETAILED DESCRIPTION

Figure 1:
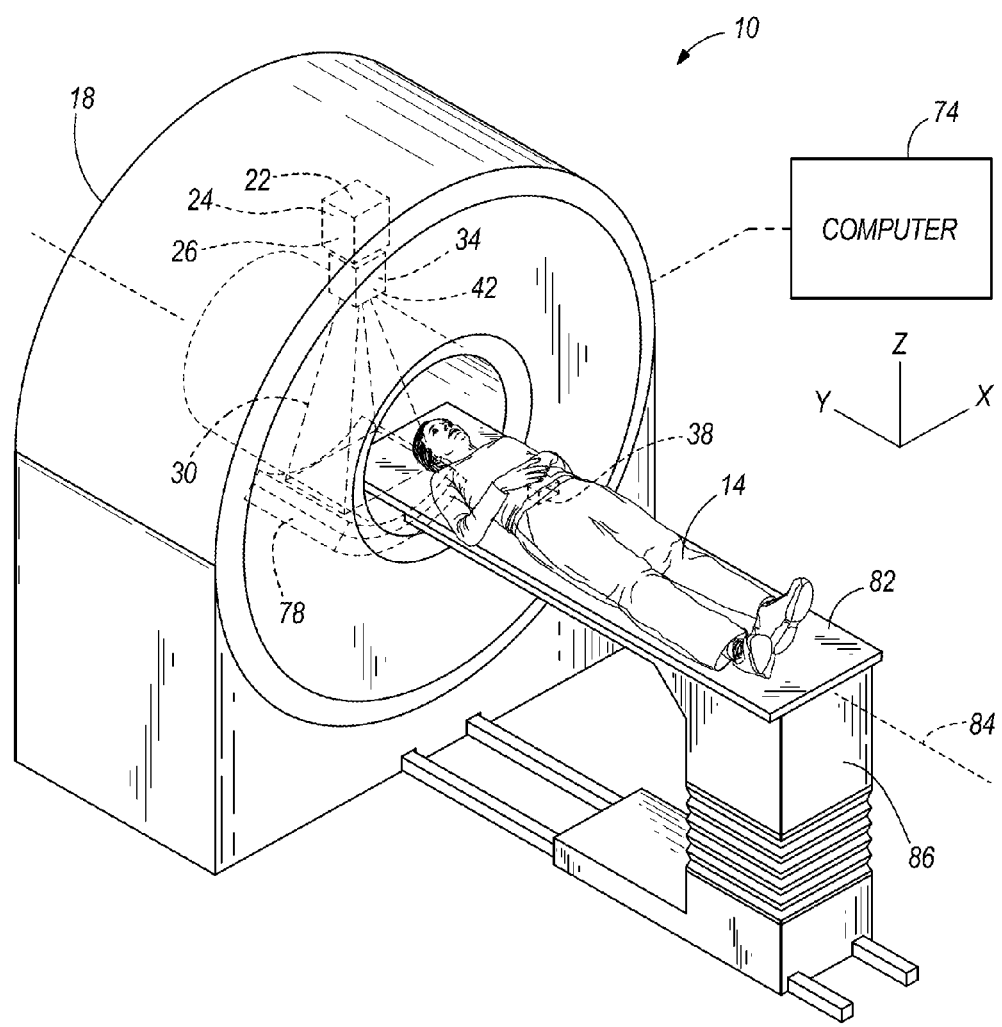
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second", and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 (a.k.a. "a linac") operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion 38 of the patient. Broadly speaking, a portion 38 may include the entire body, but is generally smaller than the entire body and can be defined by a two-dimensional area and/or a three-dimensional volume. A portion or area 38 desired to receive the radiation, which may be referred to as a target or target region, is an example of a region of interest. Another type of region of interest is a region at risk. If a portion 38 includes a region at risk, the radiation beam is preferably diverted from the region at risk. Such modulation is sometimes referred to as intensity modulated radiation therapy ("IMRT").

Figure 2:
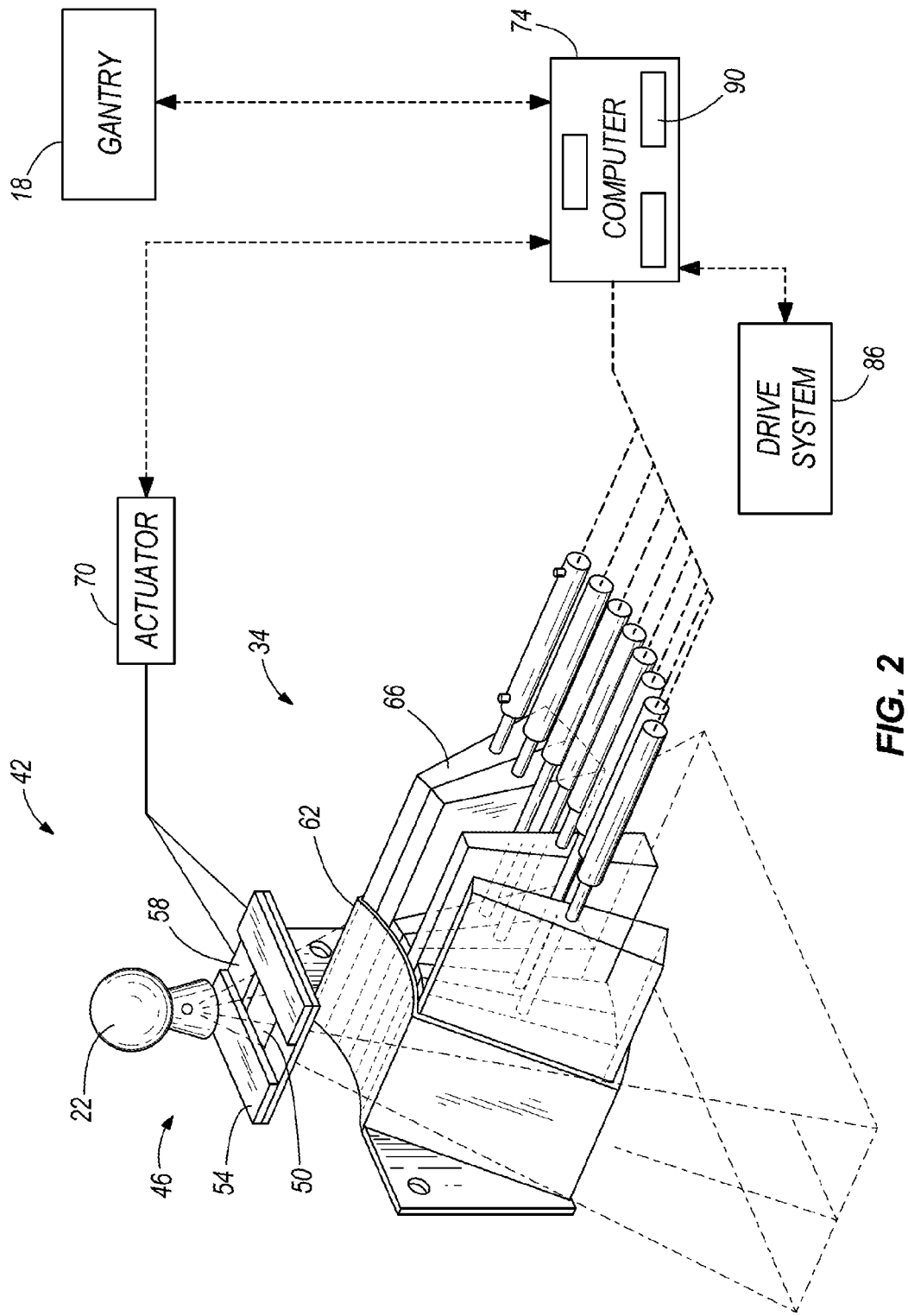
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, and illustrated in FIG. 2, the modulation device 34 can comprise a multi-leaf collimator 62 (a.k.a. "MLC"), which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30 as illustrated in FIG. 1. The linear accelerator 26 and the detector 78 can also operate as a computed tomography (CT) system to generate CT images of the patient 14. The linear accelerator 26 emits the radiation beam 30 toward the portion 38 in the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The radiation therapy treatment system 10 can also include a patient support, such as a couch 82, operable to support at least a portion of the patient 14 during treatment. While the illustrated couch 82 is designed to support the entire body of the patient 14, in other embodiments of the invention, the patient support need not support the entire body, but rather can be designed to support only a portion of the patient 14 during treatment. The couch 82 moves into and out of the field of radiation along an axis 84 (i.e., Y axis). The couch 82 is also capable of moving along the X and Z axes as illustrated in FIG. 1.

Figure 3:
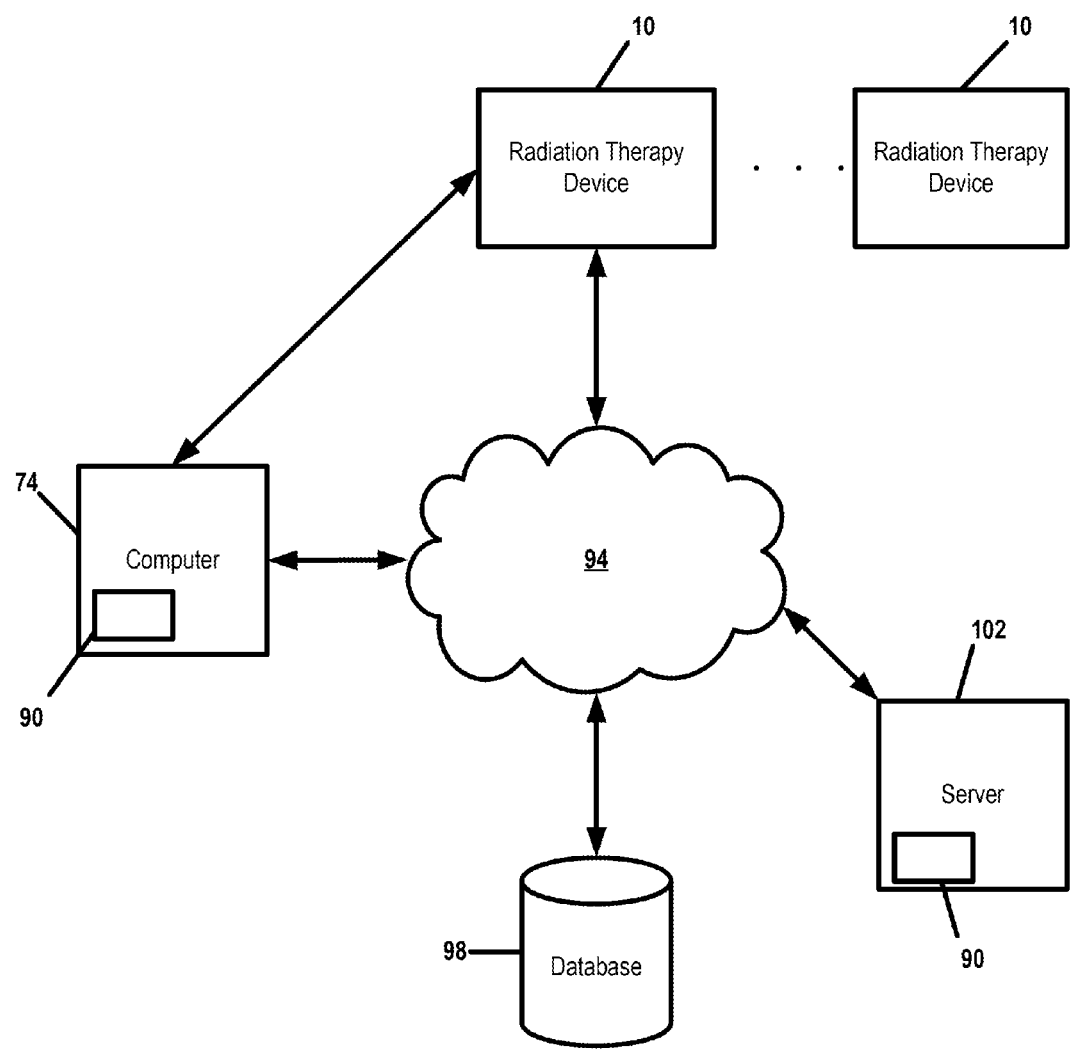
FIG. 3 is a schematic illustration of the radiation therapy treatment system of FIG. 1.

The computer 74, illustrated in FIGS. 2 and 3, includes an operating system for running various software programs (e.g., a computer readable medium capable of generating instructions) and/or a communications application. In particular, the computer 74 can include a software program(s) 90 that operates to communicate with the radiation therapy treatment system 10. The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
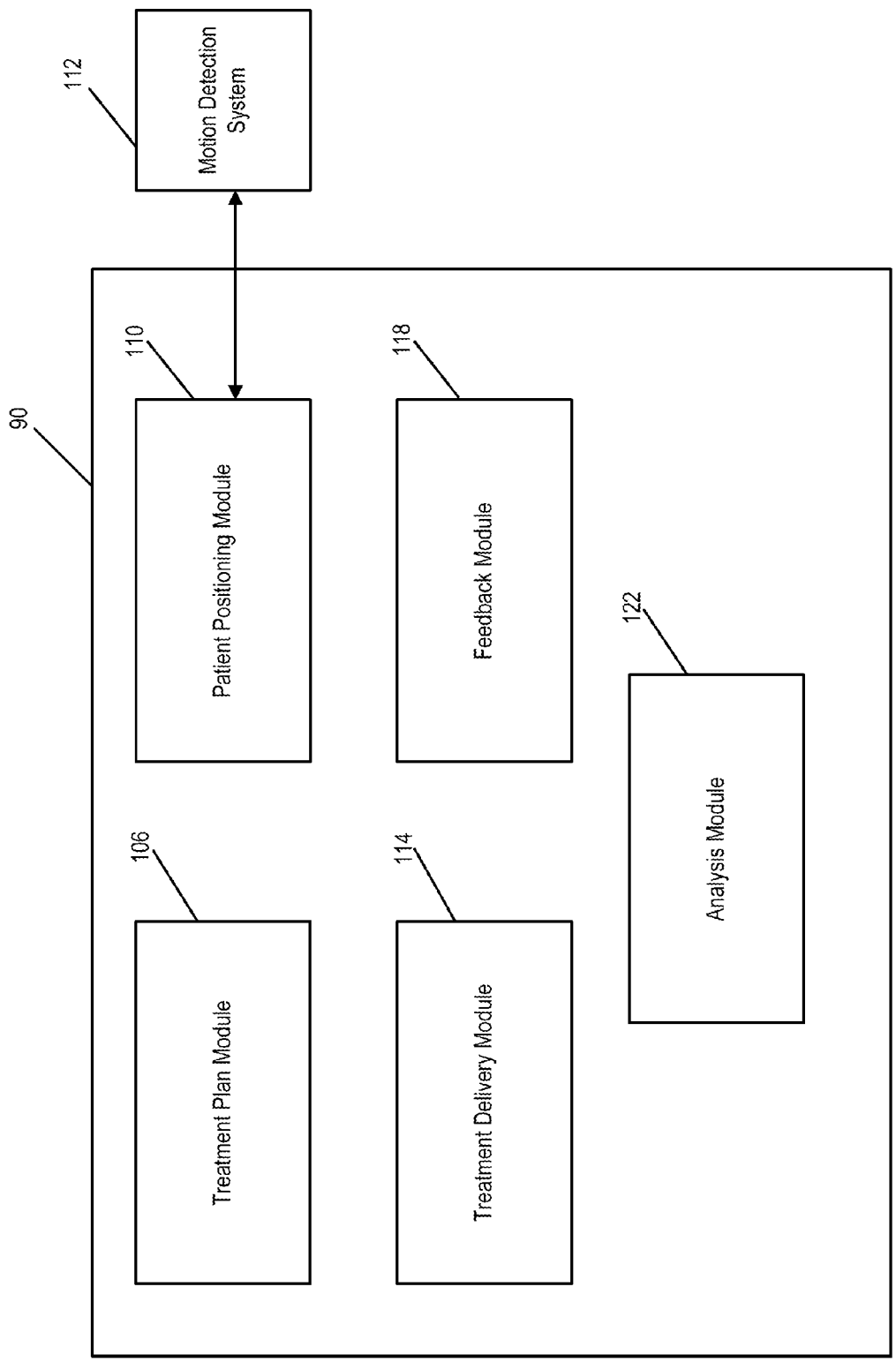
FIG. 4 is a schematic diagram of a software program used in the radiation therapy treatment system chart of a method of evaluating the delivery of a treatment plan according to one embodiment of the present invention.

The software program 90 (illustrated in block diagram form in FIG. 4) includes a plurality of modules or applications that communicate with one another to perform one or more functions of the radiation therapy treatment process. The software program 90 can transmit instructions to or otherwise communicate with various components of the radiation therapy treatment system 10 and to components and/or systems external to the radiation therapy treatment system 10. The software program 90 also generates a user interface that is presented to the user on a display, screen, or other suitable computer peripheral or other handheld device in communication with the network 94. The user interface allows the user to input data into various defined fields to add data, remove data, and/or to change the data. The user interface also allows the user to interact with the software program 90 to select data in any one or more than one of the fields, copy the data, import the data, export the data, generate reports, select certain applications to run, rerun any one or more of the accessible applications, and perform other suitable functions.

The software program 90 includes an image module 104 operable to acquire or receive images of at least a portion of the patient 14. The image module 104 can instruct the on-board image device, such as a CT imaging device to acquire images of the patient 14 before treatment commences, during treatment, and after treatment according to desired protocols. For CT images, the data comprising the patient images are composed of image elements, which represent image elements stored as data in the radiation therapy treatment system. These image elements may be any data construct used to represent image data, including two-dimensional pixels or three-dimensional voxels.

In one aspect, the image module 104 acquires an image of the patient 14 while the patient 14 is substantially in a treatment position. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The acquired images can be used for registration/alignment of the patient 14 with respect to the gantry or other point and/or to determine or predict a radiation dose to be delivered to the patient 14. The acquired images also can be used to generate a deformation map to identify the differences between one or more of the planning images and one or more of the pre-treatment (e.g., a daily image), during-treatment, or after-treatment images. The acquired images also can be used to determine a radiation dose that the patient 14 received during the prior treatments. The image module 104 also is operable to acquire images of at least a portion of the patient 14 while the patient is receiving treatment to determine a radiation dose that the patient 14 is receiving in real-time.

The software program 90 includes a treatment plan module 106 operable to generate a treatment plan, which defines a treatment regimen for the patient 14 based on data input to the system 10 by medical personnel. The data can include one or more images (e.g., planning images and/or pre-treatment images) of at least a portion of the patient 14. These images may be received from the image module 104 or other imaging acquisition device. The data can also include one or more contours received from or generated by a contour module 108. During the treatment planning process, medical personnel utilize one or more of the images to generate one or more contours on the one or more images to identify one or more treatment regions or avoidance regions of the portion 38. The contour process can include using geometric shapes, including three-dimensional shapes to define the boundaries of the treatment region of the portion 38 that will receive radiation and/or the avoidance region of the portion 38 that will receive minimal or no radiation. The medical personnel can use a plurality of predefined geometric shapes to define the treatment region(s) and/or the avoidance region(s). The plurality of shapes can be used in a piecewise fashion to define irregular boundaries. The treatment plan module 106 can separate the treatment into a plurality of fractions and can determine the amount of radiation dose for each fraction or treatment (including the amount of radiation dose for the treatment region(s) and the avoidance region(s)) based at least on the prescription input by medical personnel.

The software program 90 can also include a contour module 108 operable to generate one or more contours on a two-dimensional or three-dimensional image. Medical personnel can manually define a contour around a target 38 on one of the patient images. The contour module 108 receives input from a user that defines a margin limit to maintain from other contours or objects. The contour module 108 can include a library of shapes (e.g., rectangle, ellipse, circle, semi-circle, half-moon, square, etc.) from which a user can select to use as a particular contour. The user also can select from a free-hand option. The contour module 108 allows a user to drag a mouse (a first mouse dragging movement or swoop) or other suitable computer peripheral (e.g., stylus, touchscreen, etc.) to create the shape on a transverse view of an image set. An image set can include a plurality of images representing various views such as a transverse view, a coronal view, and a sagittal view. The contour module 108 can automatically adjust the contour shape to maintain the user-specified margins, in three dimensions, and can then display the resulting shape. The center point of the shape can be used as an anchor point. The contour module 108 also allows the user to drag the mouse a second time (a second consecutive mouse dragging movement or swoop) onto a coronal or sagittal view of the image set to create an "anchor path." The same basic contour shape is copied or translated onto the corresponding transverse views, and can be automatically adjusted to accommodate the user-specified margins on each view independently. The shape is moved on each view so that the new shape's anchor point is centered on a point corresponding to the anchor path in the coronal and sagittal views. The contour module 108 allows the user to make adjustments to the shapes on each slice. The user may also make adjustments to the limits they specified and the contour module 108 updates the shapes accordingly. Additionally, the user can adjust the anchor path to move individual slice contours accordingly. The contour module 108 provides an option for the user to accept the contour set, and if accepted, the shapes are converted into normal contours for editing.

During the course of treatment, the patient typically receives a plurality of fractions of radiation (i.e., the treatment plan specifies the number of fractions to irradiate the tumor). For each fraction, the patient is registered or aligned with respect to the radiation delivery device. After the patient is registered, a daily pre-treatment image (e.g., a 3D or volumetric image) is acquired while the patient remains in substantially a treatment position. The pre-treatment image can be compared to previously acquired images of the patient to identify any changes in the target 38 or other structures over the course of treatment. The changes in the target 38 or other structures is referred to as deformation. Deformation may require that the original treatment plan be modified to account for the deformation. Instead of having to recontour the target 38 or the other structures, the contour module 114 can automatically apply and conform the preexisting contours to take into account the deformation. To do this, a deformation algorithm (discussed below) identifies the changes to the target 38 or other structures. These identified changes are input to the contour module 114, which then modifies the contours based on those changes.

The software program 90 can also include a deformation module 110 operable to deform an image(s) while improving the anatomical significance of the results. The deformation of the image(s) can be used to generate a deformation map to identify the differences between one or more of the planning images and one or more of the daily images.

The deformed image(s) also can be used for registration of the patient 14 and/or to determine or predict a radiation dose to be delivered to the patient 14. The deformed image(s) also can be used to determine a radiation dose that the patient 14 received during the prior treatments or fractions. The image module 104 also is operable to acquire one or images of at least a portion of the patient 14 while the patient is receiving radiation treatment that can be deformed to determine a radiation dose that the patient 14 is receiving in real-time.

The software program 90 also includes a patient positioning module 112 operable to position and align the patient 14 with respect to the isocenter of the gantry 18 for a particular treatment fraction. While the patient is on the couch 82, the patient positioning module 112 acquires an image of the patient 14 and compares the current position of the patient 14 to the position of the patient in a reference image. The reference image can be a planning image, any pre-treatment image, or a combination of a planning image and a pre-treatment image. If the patient's position needs to be adjusted, the patient positioning module 112 provides instructions to the drive system 86 to move the couch 82 or the patient 14 can be manually moved to the new position. In one construction, the patient positioning module 112 can receive data from lasers positioned in the treatment room to provide patient position data with respect to the isocenter of the gantry 18. Based on the data from the lasers, the patient positioning module 112 provides instructions to the drive system 86, which moves the couch 82 to achieve proper alignment of the patient 14 with respect to the gantry 18. It is noted that devices and systems, other than lasers, can be used to provide data to the patient positioning module 112 to assist in the alignment process.

The patient positioning module 112 also is operable to detect and/or monitor patient motion during treatment. The patient positioning module 112 may communicate with and/or incorporate a motion detection system 114, such as x-ray, in-room CT, laser positioning devices, camera systems, spirometers, ultrasound, tensile measurements, chest bands, and the like. The patient motion can be irregular or unexpected, and does not need to follow a smooth or reproducible path.

The software program 90 also includes a treatment delivery module 116 operable to instruct the radiation therapy treatment system 10 to deliver the treatment plan to the patient 14 according to the treatment plan. The treatment delivery module 116 can generate and transmit instructions to the gantry 18, the linear accelerator 26, the modulation device 34, and the drive system 86 to deliver radiation to the patient 14. The instructions coordinate the necessary movements of the gantry 18, the modulation device 34, and the drive system 86 to deliver the radiation beam 30 to the proper target in the proper amount as specified in the treatment plan.

The treatment delivery module 116 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 116 can utilize canonical, predetermined or template leaf patterns to generate the appropriate pattern for the radiation beam 30 based on the treatment parameters. The treatment delivery module 116 can also include a library of patterns for typical cases that can be accessed in which to compare the present patient data to determine the pattern for the radiation beam 30.

The software program 90 also includes a feedback module 118 operable to receive data from the radiation therapy treatment system 10 during a patient treatment. The feedback module 118 can receive data from the radiation therapy treatment device and can include information related to patient transmission data, ion chamber data, MLC data, system temperatures, component speeds and/or positions, flow rates, etc. The feedback module 118 can also receive data related to the treatment parameters, amount of radiation dose the patient received, image data acquired during the treatment, and patient movement. In addition, the feedback module 118 can receive input data from a user and/or other sources. The feedback module 118 acquires and stores the data until needed for further processing.

The feedback module 118 can obtain feedback from encoders and sensors positioned on various subsystems and/or components (such as the MLC, gantry, couch, and jaws) of the radiation therapy treatment system 10. The encoders and sensors can provide feedback by detecting or determining position, velocity, and/or acceleration data. For each of these subsystems, a mathematical model is applied to the feedback (with or without additional data) which allows the feedback module 118 to derive or determine a dosimetric error from this feedback. With aggregate "real-time" data from all such subsystems combined with treatment plan information, such as patient CT data, dose output from dose monitor chambers, and other treatment plan parameters, the feedback module 118 can compute a calculated delivered dose as well as delivered dose error. The delivered dose error can be mathematically simplified for low cost implementation.

There are three potential applications for the use of calculated delivered dose and delivered dose error: (1) dosimetric tolerancing, (2) system dosimetric servo, and (3) delivery verification using real-time feedback.

Dosimetric Tolerancing

Most control systems use a predefined fixed tolerance to determine when the system is performing according to specification. This may be a calibrated value or hard-coded into the system. For example, the current Hi-Art® treatment couch uses a 1 mm tolerance defined in the software program to determine when it is within specification during treatment.

A dosimetric tolerance uses a model of expected dose in conjunction with real-time encoder feedback to compute a dosimetric error. A single dose tolerance calculation system may take real-time feedback from all modulated subsystems in the machine and derive a calculated delivered dose and delivered dose error based on treatment plan information and model of how each subsystem affects overall treatment dose. This calculated dose can provide a better understanding of the quality of the patient treatment and be used to determine that the system is operating within dosimetric tolerance.

System Dosimetric Servo

A servo system utilizes a feedback signal such as an encoder to determine its position, computes an error value, then uses this to adjust motor torque or speed to remove the error. This may also be described as a closed loop system or PID.

Each modulated subsystem in the Hi-Art® treatment system (MLC, gantry, couch, jaws) utilizes some form of servo control to maintain correct position, velocity, and acceleration during treatment. The position feedback is primarily a combination of incremental and absolute encoder feedback. While a given subsystem may exhibit a certain amount of error, there is no understanding of the impact of this error to the overall dose delivered to the patient.

The concept of system dosimetric servo involves using a real-time calculated delivered dose as defined above to determine dosimetric error as feedback. A dosimetric servo program uses this dose error and a mathematical model of dose (PID) to make adjustments to subsystems to correct the dose and minimize the dose error.

Delivery Verification Using Real-Time Feedback

With a model of delivered dose derived from each modulated subsystem in the Hi-Art® system as described above, verification of delivered dose may be performed in real-time during treatment delivery. Using treatment plan parameters such as a CT image in conjunction with real-time feedback from modulated subsystems (MLC, gantry, couch, jaws), delivered dose can be calculated at any point in time and compared to the prescribed dose. Accumulated delivered dose may be calculated during treatment delivery and saved to disk and/or memory for later delivery verification or plan adaptation.

The software program 90 also includes an analysis module 122 operable to analyze the data from the feedback module 118 to determine whether delivery of the treatment plan occurred as intended and to validate that the planned delivery is reasonable based on the newly-acquired data. The analysis module 122 can also determine, based on the received data and/or additional inputted data, whether a problem has occurred during delivery of the treatment plan. For example, the analysis module 122 can determine if the problem is related to an error of the radiation therapy treatment device 10, an anatomical error, such as patient movement, and/or a clinical error, such as a data input error. The analysis module 122 can detect errors in the radiation therapy treatment device 10 related to the couch 82, the device output, the gantry 18, the multi-leaf collimator 62, the patient setup, and timing errors between the components of the radiation therapy treatment device 10. For example, the analysis module 122 can determine if a couch replacement was performed during planning, if fixation devices were properly used and accounted for during planning, and if position and speed are correct during treatment delivery. The analysis module 122 can determine whether changes or variations occurred in the output parameters of the radiation therapy treatment device 10. With respect to the gantry 18, the analysis module 122 can determine if there are errors in the speed and positioning of the gantry 18. The analysis module 122 can receive data to determine if the multi-leaf collimator 62 is operating properly. For example, the analysis module 122 can determine if the leaves 66 move at the correct times, if any leaves 66 are stuck in place, if leaf timing is properly calibrated, and whether the leaf modulation pattern is correct for any given treatment plan. The analysis module 122 also can validate patient setup, orientation, and position for any given treatment plan. The analysis module 122 also can validate that the timing between the gantry 18, the couch 62, the linear accelerator 26, and the leaves 66 are correct.

The analysis module 122 can also utilize deformable registration data to ensure that the patient 14 is receiving the correct radiation dose across multiple fractions. When analyzing the doses, it is useful to accumulate the dose across multiple treatment fractions to determine if any errors are being exacerbated or if they are mitigating each other. Registration is a method for determining the correlation between locations of a patient's anatomy or physiology across multiple images. Deformable registration is a method of determining the correlation between locations of a patient's anatomy or physiology to account for non-rigid changes in anatomy between the images, phases, or times. The radiation dose delivered to the patient 14 is recalculated based upon on-line images and feedback from the radiation therapy treatment device 10 to ensure that the correct dose has been or is being delivered to the patient 14.

The analysis module 122 also can utilize data related to deformation-based contouring of images for quality assurance purposes. Deformable registration techniques can be used to generate automatic or semi-automatic contours for new images. Generally, a contour set has been defined for planning or other baseline patient images, but with new images, a contour set is not usually readily available. Rather than require an operator to manually contour the image, it can be both faster and more consistent to perform a deformable image registration, and then use the deformation results as the basis for modifying the original contour set to reflect the new patient anatomy. A similar family of template-based contouring algorithms has been developed to generate contours for newly available images, based upon previously available sets of images and contours. These template-based algorithms might contour a new patient image based upon a previous patient image and contour, or potentially based upon a canonical or atlas patient image and contour. This can be performed for adaptive therapy as a means to accumulate doses in daily images, each with automatic daily contours. Moreover, whereas previously these algorithms were used in the context of generating new contours based upon canonical or atlas images, it is a new aspect of this invention to apply these techniques to the particular wealth of image data and types of images that arise during image-guided radiotherapy. Specifically, this includes deformation and template-based contouring of multiple images of the same patient in which contour sets might only exist for one of the images. These multiple images of the patient may arise from use of an on-line or in-room patient imaging system, with images potentially taken on different days, or these images might derive from a "4D" imaging system such as a CT scanner, in which each image represents a phase of motion, such as a breathing phase. It should also be noted that the on-line or in-room imaging system might be the same, a similar, or a different modality from the reference image. For example, the reference image might be a CT image, whereas the on-line image could be CT, cone-beam CT, megavoltage CT, MRI, ultrasound, or a different modality. By porting these contouring techniques to the applications of quality assurance and adaptive therapy, it is possible to both save a considerable amount of time from the contouring of images, and this method can also improve the consistency of contours across multiple images of the same patient (taken at different times or representing different phases). It is known that manual contours can suffer from irreproducibility, whereas automatically generated contours can potentially be more consistent in applying the principles of an initial contour to the generation of subsequent contours.

Another benefit of the contouring process using deformable registration techniques is that the contours generated can provide a validation of the deformation process. If the generated contours closely reflect contours that one would manually draw, then it is a good indication that the deformation process is reasonable; whereas if the automatic contours are less relevant, it indicates to the user that perhaps the deformation is inappropriate, but also provides the user an opportunity to verify the manual contours to check for mistakes or inconsistencies. Another aspect of this method is that the deformation-based contours can be used as a rough-draft of the contours for the adaptive process, and manually edited to reflect the desired contours for the on-line images. When doing this, the deformation process can then be re-run, constraining the deformation map to match the initial contours to the manually-edited automatic contours, and this helps direct consistent results through the rest of the image.

The analysis module 122 also is operable to utilize deformation maps to perform dose calculations on various images for quality assurance purposes. A deformation map can be utilized to relate a plurality of images where one image is a planning image that is useful for dose calculation, and another image, such as an on-line image, has qualitative value but less direct utility for dose calculation. This relation could then be used to "remap" the more quantitative image to the qualitative shape of the on-line or less quantitative image. The resulting remapped image would be more appropriate than either of the other two images for dose calculation or quantitative applications as it would have the quantitative benefits of the first image, but with the updated anatomical information as contained in the second image. This could be useful in a variety of cases, such as where the first image (e.g., a planning image) is a CT and where the additional image lacks quantitative image values (e.g., MRI, PET, SPECT, ultrasound, or non-quantitative CT, etc. images). A similar application of this method would be to correct for geometrical distortion, imperfections, and/or incompleteness in lieu of, or in addition to, quantitative limitations. For example, a current MRI image that well represents anatomy but includes geometric distortion might be remapped to a CT image that is not distorted. Or multiple images could be used to simultaneously correct for both distortion while representing anatomical changes.

As noted above, it is important to be able to recalculate dose on patient images acquired after the planning image. Given these doses, it is also useful to accumulate these doses for multiple delivered fractions. These doses can be added based upon the location of the doses in physical space, but a better method is to incorporate deformation methods into the process so as to add doses based upon the structures that received the dose, even if the structures have changed location. However, it is possible to build upon this technology to perform novel types of adaptive therapy.

In the context of recalculating doses, there are several other aspects of this invention to improve or facilitate this process. For example, after recording any daily registrations applied to the patient, potentially based upon image-guidance, these same registrations can optionally be applied to the patient images when recalculating dose. This can be performed automatically or semi-automatically. Alternately, the dose could be recalculated with a different registration. The benefit is that by automatically using the recorded registrations, the process of recalculating the doses that were delivered is simplified and streamlined. Moreover, by having the ability to recalculate doses for different registrations, one can experiment to determine if other patient alignment protocols might have been more or less effective. And by not using the recorded registration, one can determine how the treatment would have been affected in the absence of image guidance.

The dose recalculation process also can be enhanced by the padding of incomplete images. This is because a limited-size image, whether limited in the axial plane and/or in the superior/inferior direction, can degrade the accuracy of dose calculations. A method to overcome this is to pad the limited-size image with other image data, such as from the planning image. This padding method can work for both axially or superior/inferior limited data. In addition, another method for padding superior/inferior data is to repeat the end slices of the incomplete image as necessary until the data is sufficiently large for improved dose calculation.

Additional aspects of dose recalculation entail the calculation of dose to account for true 4D motion. Previous teachings describe methods for generating "4D CT" images, which are a time-based series of images or a collection of 3D image volumes that each represents a "phase" of a motion pattern, such as breathing. These images have been used for contouring, and even for generating treatment plans that anticipate a certain cycle of "phases". However, patient breathing can often deviate from the ideally reproducible pattern indicated by a "4D CT" image set. The invention provides a method to recalculate dose more accurately on one of these volumes. This entails using a motion detection system 114 to monitor the patient's motion during treatment. This motion can be irregular or unexpected, and need not follow a smooth or reproducible trajectory. And the motion can be detected with any of a number of monitoring systems including x-ray, in-room CT, laser positioning devices, camera systems, spirometers, ultrasound, tensile measurements, or the like. Given these measurements, the dose can be recalculated for the patient's actual delivery by using the measured data to indicate the phase the patient was in at any given time, and recalculating the dose for each time in the phase of the 4D CT image best matching the patient's instantaneous position. This can also be performed using CT images collected simultaneously with patient treatment. In this latter case, phase identification might not be necessary. In one embodiment, deformation techniques would be used to accumulate doses between the different phases or images. In addition, the generation of updated 4D CT images before or during treatment could be used in conjunction with this method, as could other types of 4D images that are not strictly CT, such as 4D PET or 4D MRI, although these would typically require some modification to use these images quantitatively.

One application of this technology is to correct for poor treatments, such as what could result from poor planning, or poor delivery of a plan. The analysis module 122 can analyze the net dose delivered, and generate corrective plans to deliver the net desired dose or a dose chosen to match the intended biological effect. The original treatments would not need to be limited to photon-based radiation therapy, but could be any form of treatment including brachytherapy, electron beam therapy, proton, neutron, or particle therapy, or other types of treatments.

Another aspect of this invention is that the concept of adaptive therapy can be applied not only based upon the doses received alone, but also on predicted trends in the patient's treatment, clinical results, machine changes, and/or biological markers. For example, if a trend is detected in that a tumor is shrinking, or that a normal tissue structure is gradually migrating, the adaptive planning process could not only account for the current status of the patient and the doses delivered to date, but could also generate plans that reflect anticipated further changes in anatomy. Similarly, when analyzing cumulative dose information during the course of a treatment, the clinician can also consider the level of clinical effects and side-effects that the patient is experiencing, either based upon clinical findings or available biological markers or tests. If few side effects are felt, a more aggressive adaptive therapy treatment might be pursued, whereas if more complications are detected, the therapy might be modified to better avoid the affected region. Furthermore, plans can be adapted to compensate for detected changes in the machine, such as variations in output, energy, or calibration.

A variation of this theme is to perform a radiobiopsy. Early in a treatment, or before radiation treatment fully begins, the patient may receive a treatment fraction with a high radiation dose to a localized region, or potentially a dose only to a localized region. The effects on this region can be monitored to determine the nature of that region, such as whether it is tumorous, and what type. An appropriate course of treatment can be determined based upon these results, and the dose already delivered can be incorporated into the planning process.

Figure 5:
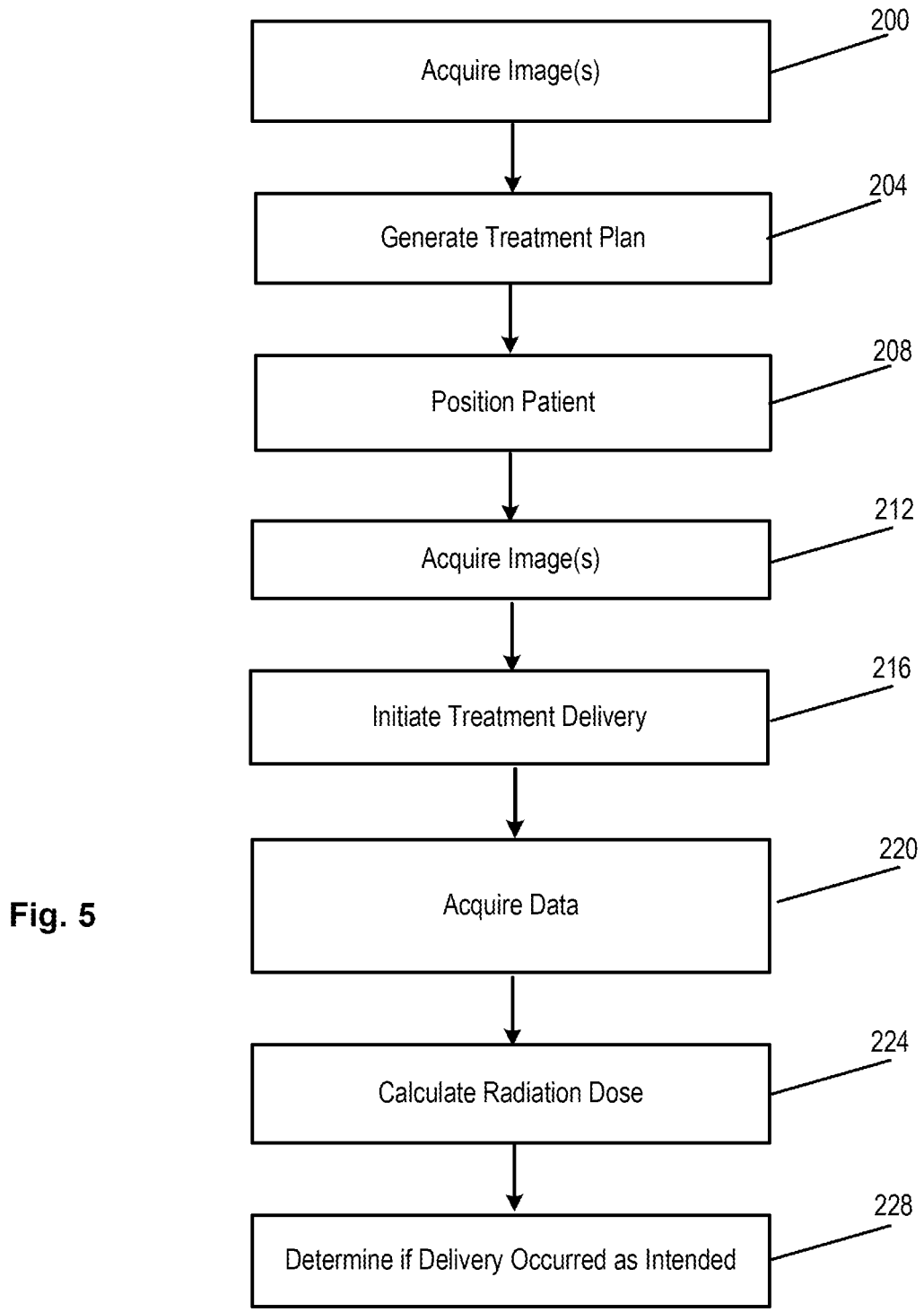
FIG. 5 is a flow chart of a method of verifying system-level quality assurance according to one embodiment of the present invention.

FIG. 5 illustrates a flow chart of a method of verifying system-level quality assurance. Medical personnel acquire (at 200) an image of the patient and generate (at 204) a treatment plan for the patient 14 based on patient data, images, or other information. When the patient 14 is ready for a treatment, medical personnel position (at 208) the patient 14 on the couch 82 with the assistance of the patient positioning module 112 prior to delivery of treatment. Medical personnel initiate (at 212) acquisition of an on-line image of the patient 14 to assist in the positioning or alignment process. Additional positioning adjustments can be made as necessary. After the patient 14 is properly positioned, the user initiates (at 216) the treatment according to the treatment plan with the assistance of the treatment delivery module 116. During delivery of the treatment plan, the feedback module 118 acquires (at 220) data related to the radiation therapy treatment device 10 and patient parameters. During and/or after treatment, the analysis module 122 calculates (at 224) a radiation dose received by the patient 14 and determines (at 228) whether the delivery of the treatment plan occurred as intended.

Figure 6:
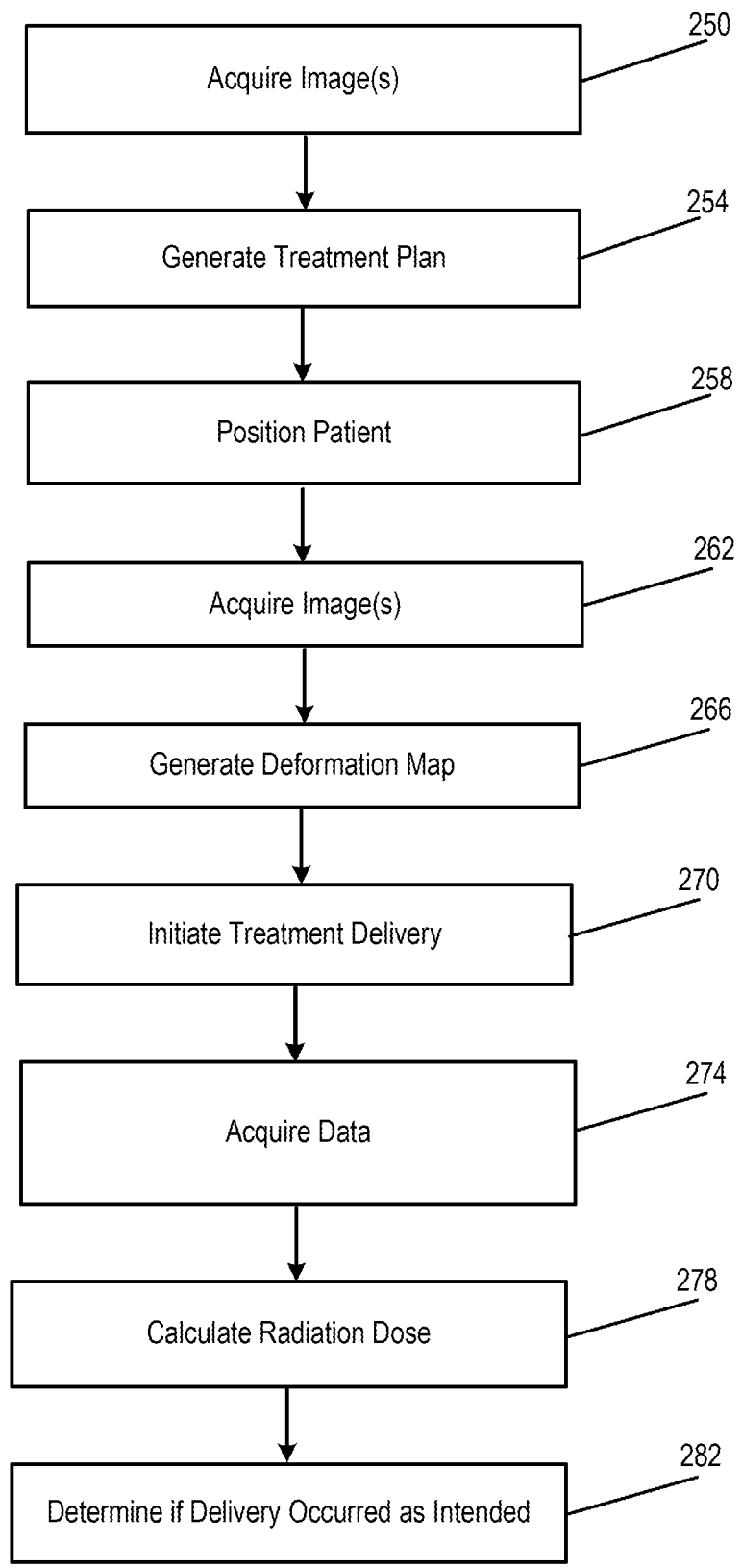
FIG. 6 is a flow chart of a method of verifying system-level quality assurance according to one embodiment of the present invention.

FIG. 6 illustrates a flow chart of a method of verifying system-level quality assurance. Medical personnel acquire (at 250) an image of the patient and generate (at 254) a treatment plan for the patient 14 based on patient data, images, or other information. When the patient 14 is ready for a treatment, medical personnel position (at 258) the patient 14 on the couch 82 with the assistance of the patient positioning module 112 prior to delivery of treatment. Medical personnel initiate (at 262) acquisition of an on-line image of the patient 14 to assist in the positioning process. Additional positioning adjustments can be made as necessary. Medical personnel initiate (at 266) generation of a deformation map between one of the images in the treatment plan and the on-line image. After the patient 14 is properly positioned, the user initiates (at 270) the treatment according to the treatment plan with the assistance of the treatment delivery module 116. During delivery of the treatment plan, the feedback module 118 acquires (at 274) data related to the radiation therapy treatment device 10 and patient parameters. During and/or after treatment, the analysis module 122 calculates (at 278) a radiation dose received by the patient 14 and determines (at 282) whether the delivery of the treatment plan occurred as intended.

Various features and advantages of the invention are set forth in the following claims.

What is claimed is:

1. A method of determining whether a component of a radiation therapy system is operating within a dosimetric tolerance, the method comprising:
   generating a treatment plan for a patient, the treatment plan specifying a radiation amount to be delivered to the patient;
   delivering radiation to the patient according to the treatment plan;
   obtaining feedback during the delivery of radiation, the feedback related to one of a position, a velocity, and an acceleration for one of a multi-leaf collimator, a gantry, a couch, and a jaws;
   generating a mathematical model based on the feedback for one of the multi-leaf collimator, the gantry, the couch, and the jaws;
   calculating a delivered dose amount based on the mathematical model and treatment plan information;
   calculating a deviation in dose between the radiation amount specified in the treatment plan and the delivered dose amount; and
   determining whether the deviation in dose is within a dosimetric tolerance for the one of the multi-leaf collimator, the gantry, the couch, and the jaws.

2. A method of determining whether a component of a radiation therapy system deviated from specified operation, the method comprising:
   generating a treatment plan for a patient, the treatment plan specifying a radiation amount to be delivered to the patient;
   delivering radiation to the patient according to the treatment plan;
   obtaining feedback during the delivery of radiation, the feedback related to one of a position, a velocity, and an acceleration for one of a multi-leaf collimator, a gantry, a couch, and a jaws;
   calculating a delivered dose amount based on the feedback;
   calculating a deviation in dose between the radiation amount specified in the treatment plan and the delivered dose amount; and
   adjusting one of the multi-leaf collimator, the gantry, the couch, and the jaws to minimize the deviation in dose.

* * * * *